(12) United States Patent
Buchberger et al.

(10) Patent No.: US 11,413,410 B2
(45) Date of Patent: Aug. 16, 2022

(54) ELECTRONIC AEROSOL PROVISION SYSTEM

(71) Applicant: NICOVENTURES HOLDINGS LIMITED, London (GB)

(72) Inventors: Helmut Buchberger, St. Florian (AT); Colin Dickens, London (GB); Rory Fraser, London (GB)

(73) Assignee: NICOVENTURES TRADING LIMITED, London (GB)

( * ) Notice: Subject to any disclaimer, the term of this patent is extended or adjusted under 35 U.S.C. 154(b) by 654 days.

(21) Appl. No.: 15/506,594

(22) PCT Filed: Aug. 7, 2015

(86) PCT No.: PCT/GB2015/052290
§ 371 (c)(1),
(2) Date: Feb. 24, 2017

(87) PCT Pub. No.: WO2016/030661
PCT Pub. Date: Mar. 3, 2016

(65) Prior Publication Data
US 2017/0251725 A1    Sep. 7, 2017

(30) Foreign Application Priority Data

Aug. 26, 2014 (GB) .................... 1415051

(51) Int. Cl.
*A61M 15/06* (2006.01)
*A61M 11/04* (2006.01)
(Continued)

(52) U.S. Cl.
CPC .......... *A61M 15/06* (2013.01); *A24B 15/167* (2016.11); *A24F 40/53* (2020.01); *A61M 11/042* (2014.02);
(Continued)

(58) Field of Classification Search
CPC ... A24F 47/008; A61M 11/042; A61M 15/06; A61M 2205/18; A61M 2205/44;
(Continued)

(56) References Cited

U.S. PATENT DOCUMENTS 6,080,973 A    6/2000 Thweatt
6,803,550 B2   10/2004 Sharpe
(Continued)

FOREIGN PATENT DOCUMENTS

AU    2015308301 B2    3/2018
CN    203166461 U     8/2013
(Continued)

OTHER PUBLICATIONS

GB Search Report, Application No. GB1415051.0, dated Feb. 26, 2015, 5 pages.
(Continued)

*Primary Examiner* — Dana Ross
*Assistant Examiner* — Joe E Mills, Jr.
(74) *Attorney, Agent, or Firm* — Patterson Thuente Pedersen, P.A.

(57) ABSTRACT

An aerosol provision system comprises a heating element for generating an aerosol from a source liquid and control circuitry for controlling a supply of electrical power from a power supply to the heating element. The control circuitry is configured to measure an indication of a derivative of an electrical characteristic of the heating element with respect to time. Based on the measured time derivative, the control circuitry is configured to determine whether or not a fault condition has arisen for the electronic aerosol provision system. The overall change in the electrical characteristic for the heating element caused by the localized heating may be small and so difficult to reliably identify, but the rate at which the change occurs can be expected to be relatively (Continued)

high, such that the time derivative of the local characteristic is a more reliable indicator of occurrence of the fault condition.

20 Claims, 3 Drawing Sheets

(51) Int. Cl.
    *A24F 40/53* (2020.01)
    *A24B 15/167* (2020.01)
    *H05B 1/02* (2006.01)
    *A61M 16/00* (2006.01)
    *A24F 40/10* (2020.01)
    *A24F 40/46* (2020.01)

(52) U.S. Cl.
    CPC ............ *H05B 1/0244* (2013.01); *A24F 40/10* (2020.01); *A24F 40/46* (2020.01); *A61M 2016/0015* (2013.01); *A61M 2016/0027* (2013.01); *A61M 2205/18* (2013.01); *A61M 2205/44* (2013.01); *A61M 2205/581* (2013.01); *A61M 2205/583* (2013.01); *A61M 2205/8206* (2013.01); *H05B 2203/021* (2013.01)

(58) Field of Classification Search
    CPC ...... A61M 2205/581; A61M 2205/583; A61M 2205/8206; A61M 2016/0015; A61M 2016/0027; A61M 2205/33; H05B 1/0244; H05B 2203/021
    USPC .......................................... 392/404, 395–398
    See application file for complete search history.

(56) References Cited

U.S. PATENT DOCUMENTS

| | | |
|---|---|---|
| 2002/0079309 A1 | 6/2002 | Cox |
| 2004/0149737 A1 | 8/2004 | Sharpe et al. |
| 2008/0092912 A1 | 4/2008 | Robinson et al. |
| 2010/0286895 A1 | 11/2010 | Bauer |
| 2011/0226236 A1 | 9/2011 | Buchberger |
| 2013/0306064 A1 | 11/2013 | Thorens |
| 2013/0306084 A1 | 11/2013 | Flick |
| 2014/0014126 A1* | 1/2014 | Peleg ............... G01K 7/16 131/329 |
| 2014/0069424 A1* | 3/2014 | Poston ............... A24F 47/008 128/202.21 |
| 2015/0164143 A1* | 6/2015 | Maas ............... A24F 40/44 131/329 |

FOREIGN PATENT DOCUMENTS

| | | |
|---|---|---|
| CN | 103338663 A | 10/2013 |
| CN | 103338665 A | 10/2013 |
| CN | 203398771 U | 1/2014 |
| EP | 0358002 A2 | 3/1990 |
| EP | 2316286 | 5/2011 |
| EP | 3154382 | 4/2017 |
| JP | 4030458 | 1/2008 |
| JP | 2014501106 A | 1/2014 |
| JP | 2017532011 A | 11/2017 |
| KR | 20130130759 A | 12/2013 |
| RU | 84708 | 7/2009 |
| RU | 129368 | 6/2013 |
| WO | WO 2011050964 | 5/2011 |
| WO | WO 2012085203 | 6/2012 |
| WO | WO-2012085205 A1 | 6/2012 |
| WO | WO 2012/109371 A2 | 8/2012 |
| WO | WO-2013098396 A2 | 7/2013 |
| WO | WO 2013098398 A1 | 7/2013 |
| WO | WO2015192084 | 12/2015 |
| WO | WO2015192084 A1 | 12/2015 |

OTHER PUBLICATIONS

International Search Report and Written Opinion, International Application No. PCT/GB2015/052290, dated Nov. 5, 2015, 11 pages.
International Preliminary Report on Patentability, Application No. PCT/GB2015/052290, dated Aug. 2, 2016, 7 pages.
Russian Office Action, Application No. 2017105568, dated Feb. 21, 2018, 6 pages.
Korean Office Action, Application No. 10-2017-7005438, dated Feb. 21, 2018, 19 pages.
Russian Decision to Grant, Application No. 2017105568, dated Jun. 20, 2018, 10 pages.
European Notice of Opposition, Application No. 15749864.3, dated Jul. 16, 2019, 41 pages.
Compact Oxford English Dictionary, 'Derivative', Oxford University Press, © 2000, 2002, 2003, 2005 and 2008, 3 pages.
Rosloniec, S. *Fundamental Numerical Methods for Electrical Engineering*, © 2008, 3 pages.
Combined Search and Examination Report under Sections 17 and 18(3) For GB Application No. GB2100840.4, dated Mar. 12, 2021, 6 pages.
Examination Report for Great Britain Application No. 1415051.0 dated Mar. 24, 2020, 3 pages.
Office Action dated Mar. 19, 2021 for Korean Application No. 10-2018-7038203, 3 pages.
Summons to Attend Oral Proceedings, European Application No. 15749864.3, dated Nov. 5, 2020, 13 pages.
U.S. Provisional Application file history, U.S. Appl. No. 62/012,312, Inventor John Joseph Bellinger, date of receipt at International Bureau dated Jun. 28, 2015, 29 pages.
EP Notice of Opposition, European Patent No. 3185941, dated Jul. 16, 2019, 27 pages.

* cited by examiner

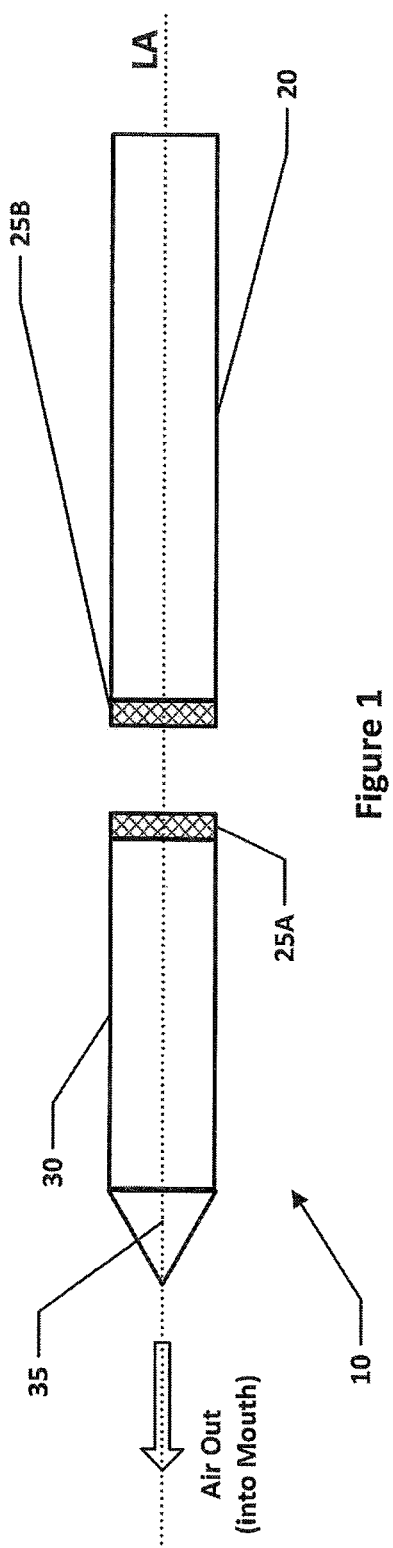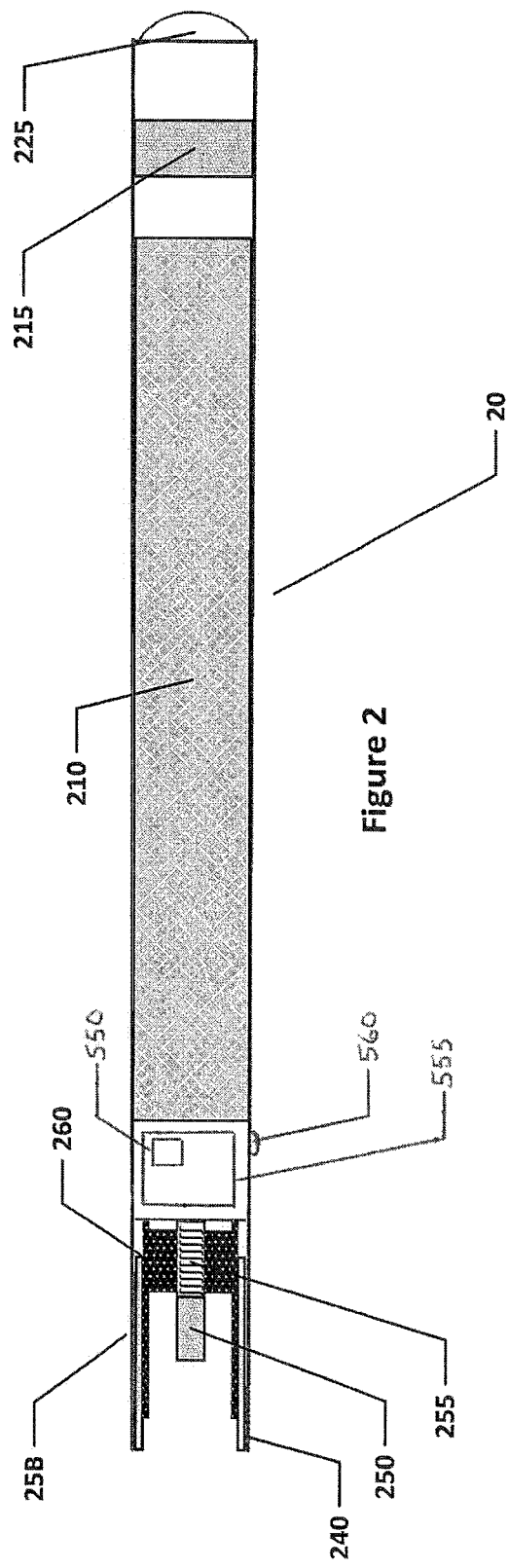

ELECTRONIC AEROSOL PROVISION SYSTEM

CROSS-REFERENCE TO RELATED APPLICATION

The present application is a National Phase entry of PCT Application No. PCT/GB2015/052290, filed Aug. 7, 2015, which claims priority from GB Patent Application No. 1415051.0, filed Aug. 26, 2014, which is hereby fully incorporated herein by reference.

TECHNICAL FIELD

The present disclosure relates to electronic aerosol provision systems such as nicotine delivery systems (e.g. e-cigarettes and the like).

BACKGROUND

Electronic aerosol provision systems such as e-cigarettes generally contain a reservoir of a source liquid containing a formulation, typically including nicotine, from which an aerosol is generated, e.g. through heat vaporization. An aerosol source for an aerosol provision system may thus comprise a heater having a heating element adjacent to a wick arranged to draw source liquid from the reservoir to the vicinity of the heating element. When a user inhales on the device, electrical power is supplied to the heating element to vaporize source liquid from the wick to generate an aerosol for inhalation by the user. Such devices are usually provided with one or more air inlet holes located away from a mouthpiece of the system. When a user sucks on the mouthpiece, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

It is known in electronic aerosol provision systems to control the power supplied to the heater's heating element to seek to provide a desired performance in terms of aerosol generation. For example, WO 2012/109371 discloses a device in which a selection of an operating mode may depend on readings from temperature sensors inside the device. US 2014/0014126 discloses a device in which the temperature of a heating element is determined from its resistance as it heats and cools to establish a thermal time constant for the device. The power supplied to the heating element may then be adjusted based on the time constant. EP 2 316 286 describes an electrically heated smoking system in which the temperature of a heating element is determined from its resistance and power is supplied to the heating element in dependence on its temperature. Aerosol provision systems may also comprise other heaters, for example US 2004/0149737 describes a device having an inductive heating system for removing condensates from electronic smoking systems in which the temperatures of an arrangement of heaters are determined from their respective electrical resistances.

The present inventor has recognized a problem with existing aerosol provision systems of the kind discussed above can arise if a portion of the wick adjacent a heating element becomes dry. This can happen, for example, because the supply of source liquid to the wick may become unstable when the reservoir is becoming empty. The inventor has recognized in particular this condition can lead to rapid heating of the heating element in the vicinity of the dry portion of the wick. The over-heating may be localized, but can also affect larger and more extended sections of the heating element. Having regard to typical operating conditions, the over-heated section/hotspot might be expected to quickly reach temperatures in the range 500 to 900° C. Not only does this degree of rapid heating potentially represent a risk of fire and burning for a user, radiant heat from the hotspot may damage components within the aerosol provision system and may affect the evaporation process adversely. For example, heat from a hotspot may cause the source liquid and/or the generated aerosol to decompose, for example through pyrolysis, which can potentially release unpleasant tasting substances into the air stream to be inhaled by a user. The heat from a hotspot may also ignite combustible vapor/air mixtures which in turn can increase the temperature of the air stream to be inhaled by a user considerably. It is not only unstable wicking that can cause over-heating and hotspots. Over-heating can also be the result of too much electrical power being provided to the heating element. If the heat flux exceeds a certain upper limit (typically around 1 W/mm$^2$), nucleate boiling may turn into film boiling, the latter boiling mechanism being much less effective, resulting in a sudden temperature rise of the heating element.

In view of the issues discussed above, there is a desire for methods and apparatus which are able to identify when there is rapid over-heating of a heating element in an aerosol provision system, thereby allowing remedial action to be taken, for example by reducing power to the heating element, for example stopping the supply of power, and/or warning a user.

SUMMARY

According to an aspect of certain embodiments, there is provided an electronic aerosol provision system comprising: a heating element for generating an aerosol from a source liquid; and control circuitry for controlling a supply of electrical power from a power supply to the heating element, and wherein the control circuitry is further configured to determine an indication of a derivative of an electrical characteristic of the heating element with respect to time; and determine whether or not a fault condition for the electronic aerosol provision system has arisen based on the determined indication of the derivative of the electrical characteristic of the heating element with respect to time.

According to another aspect of certain embodiments, there is provided a method of operating an electronic aerosol provision system comprising a heating element for generating an aerosol from a source liquid and control circuitry for controlling a supply of electrical power from a power supply to the heating element, wherein the method comprises determining an indication of a derivative of an electrical characteristic of the heating element with respect to time; and determining whether or not a fault condition for the electronic aerosol provision system has arisen based on the determined indication of the derivative of the electrical characteristic of the heating element with respect to time.

The approaches described herein are not restricted to specific embodiments such as set out below, but include and contemplate any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Various embodiments will now be described in detail by way of example only with reference to the following drawings:

FIG. 1 is a schematic (exploded) diagram of an electronic aerosol provision system such as an e-cigarette in accordance with some embodiments.

FIG. 2 is a schematic diagram of a main body portion of the e-cigarette of FIG. 1 in accordance with some embodiments.

DETAILED DESCRIPTION

Figure 3:
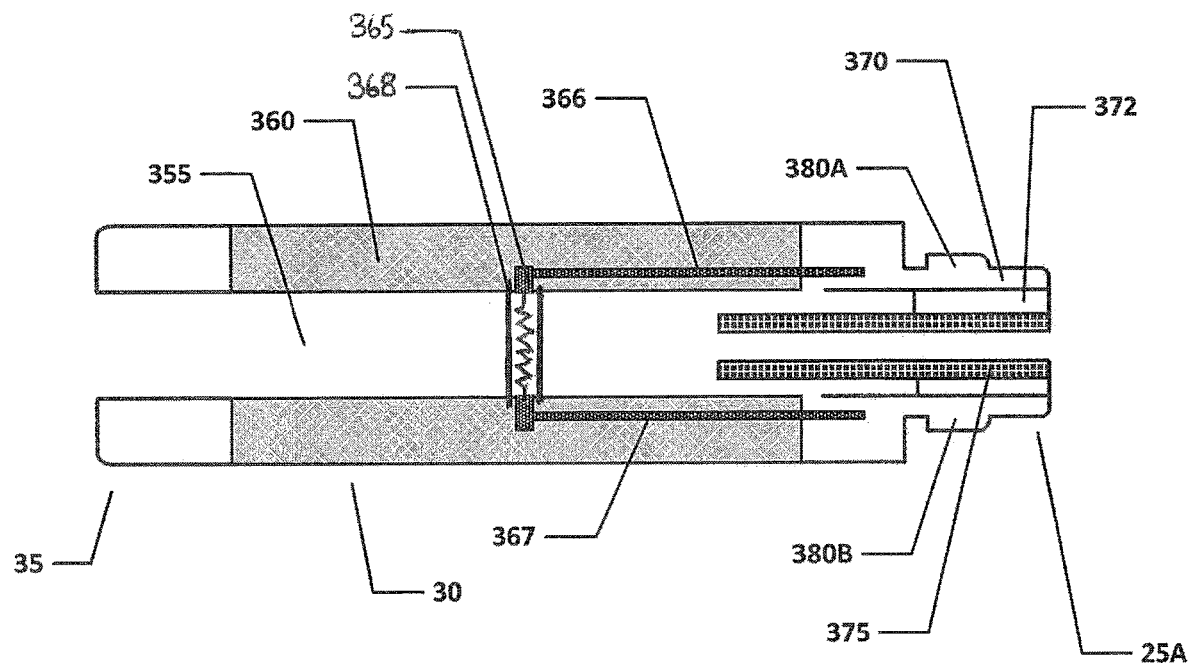
FIG. 3 is a schematic diagram of an aerosol source portion of the e-cigarette of FIG. 1 in accordance with some embodiments.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used but this term may be used interchangeably with aerosol (vapor) provision system.

FIG. 1 is a schematic diagram of an aerosol/vapor provision system such as an e-cigarette 10 in accordance with some embodiments (not to scale). The e-cigarette 10 has a generally cylindrical shape, extending along a longitudinal axis indicated by dashed line LA, and comprising two main components, namely a body 20 and a cartomizer 30. The cartomizer 30 includes an internal chamber containing a reservoir of a source liquid comprising a liquid formulation from which an aerosol is to be generated, for example containing nicotine, a heating element, and a liquid transport element (in this example a wicking element) for transporting source liquid to the vicinity of the heating element. The wicking element and the heating element may sometimes be collectively referred to as an aerosol generator/aerosol source/aerosol forming member/vaporizer/atomizer. The cartomizer 30 further includes a mouthpiece 35 having an opening through which a user may inhale the aerosol from the aerosol generator. The source liquid may be of a conventional kind used in e-cigarettes, for example comprising 0-5% nicotine dissolved in a solvent comprising glycerol, water, or/and propylene glycol. The source liquid may also comprise flavorings. The reservoir for the source liquid may comprise a porous matrix or any other structure within a housing for retaining the source liquid until such time that it is required to be delivered to the aerosol generator/vaporizer.

As discussed further below, the body 20 includes a re-chargeable cell or battery to provide power for the e-cigarette 10 and a circuit board comprising control circuitry for generally controlling the e-cigarette 10. In use, when the heating element receives power from the battery, as controlled by the circuit board, the heating element vaporizes source liquid from the wicking element at a heating location in the vicinity of the heating element to generate an aerosol. The aerosol is inhaled by a user through the opening in the mouthpiece 35. During user inhalation the aerosol is carried from the aerosol source to the mouthpiece 35 opening along an air channel that connects between them.

In this particular example, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer 30 also serves as a socket for connecting a charging device (not shown) when the body 20 is detached from the cartomizer 30. The other end of the charging device can be plugged into an external power supply, for example a USB socket, to charge or to re-charge the cell/battery in the body 20 of the e-cigarette 10. In other implementations, a cable may be provided for direct connection between the electrical connector on the body 20 and the external power supply.

The e-cigarette 10 is provided with one or more holes (not shown in FIG. 1) for air inlet. These holes connect to an air running passage through the e-cigarette 10 to the mouthpiece 35. The air passage includes a region around the aerosol source and a section comprising an air channel connecting from the aerosol source to the opening in the mouthpiece 35.

When a user inhales through the mouthpiece 35, air is drawn into this air passage through the one or more air inlet holes, which are suitably located on the outside of the e-cigarette 10. This airflow (or the resulting change in pressure) is detected by a pressure sensor that in turn activates the supply of electrical power from the battery to the heating element to vaporize a portion of the liquid source in the wicking element adjacent the heating element. Triggering the operation of the e-cigarette 10 in response to user inhalation may be implemented in accordance with conventional techniques. The airflow passes through the air passage and combines/mixes with the vapor in the region around the aerosol source to generate the aerosol. The resulting combination of airflow and vapor continues along the air channel connecting from the aerosol source to the mouthpiece 35 for inhalation by a user. The cartomizer 30 may be detached from the body 20 and disposed of when the supply of source liquid is exhausted (and replaced with another cartomizer if so desired). Alternatively, the cartomizer 30 may be refillable.

Generally, the construction and operation of the e-cigarette 10 may follow established techniques in the field of aerosol provision systems except where modified to provide functionality in accordance with the methods and apparatus described herein. It will therefore be appreciated the e-cigarette 10 shown in FIG. 1 is presented as a one example implementation of an aerosol provision system according to the present disclosure, and various other implementations can be adopted in the context of other configurations of aerosol provision system. For example, in some embodiments, the cartomizer 30 may be provided as two separable components, namely a cartridge comprising the source liquid reservoir and mouthpiece (which can be replaced when the source liquid from the reservoir is exhausted), and a vaporizer/aerosol generator comprising a heating element (which is generally retained). As another example, the charging facility and/or the heating element itself may connect to an additional or alternative power source, such as a car cigarette lighter socket. More generally, it will be appreciated that embodiments of the disclosure described herein may be implemented in conjunction with any design of electronic aerosol provision system that is based on an electronic heating element for vaporizing/aerosolizing source liquid and the underlying operating principles and structural design of other aspects of the aerosol provision system are not significant to the principles of operation in accordance with the embodiments described herein.

FIG. 2 is a schematic diagram of the body 20 of the e-cigarette 10 of FIG. 1. FIG. 2 can generally be regarded as a cross-section in a plane through the longitudinal axis LA of the e-cigarette 10. Note that various components and details of the body 20, e.g. such as wiring and more complex shaping, have been omitted from FIG. 2 for reasons of clarity.

As shown in FIG. 2, the body 20 includes a battery or cell 210 for powering the e-cigarette 10, as well as a circuit board 555 comprising control circuitry 550, in this example in the form of a chip, such as an application specific integrated circuit (ASIC) or microcontroller, for controlling the e-cigarette 10. The control circuitry 550 may be arranged alongside or at one end of the battery 210. The control circuit 550 may be provided as a single element or a number of discrete elements. The control circuitry 550 is connected to a sensor unit 215 to detect an inhalation on mouthpiece 35 (or alternatively the sensor unit 215 may be provided by the control circuitry 550 itself). In response to such a detection, the control circuitry 550 activates the supply of power from the battery or cell 210 to the heating element in the cartomizer 30 to vaporize source liquid and introduce an aerosol into the airflow which is inhaled by a user. As noted above, this aspect of the operation may be conventional. However, in addition to being configured to support the conventional operating aspects of the e-cigarette 10 in accordance with established techniques, the control circuit 550 is further configured in accordance with embodiments of the disclosure to operate to determine whether or not a fault condition (corresponding to the occurrence of a hot-spot/glowing/rapid over-heating of the heating element) has arisen, as described further below. In this regard, the body 20 of the aerosol provision system 10 in accordance with this example implementation further comprises an indicator 560 to provide a user with an indication (warning) of when a fault condition has arisen. The indicator 560 in this example comprises a light, for example a light emitting diode, which is coupled to, and may be driven by, the control circuitry 550. Other forms of indicator may be used, for example a speaker for emitting a warning tone in response to a fault condition being determined to have arisen.

The body 20 further includes a cap 225 to seal and protect the far (distal) end of the e-cigarette 10. There is an air inlet hole provided in or adjacent to the cap 225 to allow air to enter the body 20 and flow past the sensor unit 215 when a user inhales on the mouthpiece 35. This airflow therefore allows the sensor unit 215 to respond to the user inhalation to trigger the control circuitry 550 to activate the aerosol generator element of the e-cigarette 10 (i.e. to supply electrical power to the heating element).

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring 255 in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the body 20 and the cartomizer 30. The body connector 240 and the electrical contact 250 are separated by a spacer 260, which is made of a non-conductor (such as plastic) to provide good insulation between the two electrical terminals. The spacer 260 is shaped to assist with the mutual mechanical engagement of connectors 25A and 25B.

FIG. 3 is a schematic diagram of the cartomizer 30 of the e-cigarette 10 of FIG. 1 in accordance with some embodiments. FIG. 3 can generally be regarded as a cross-section in a plane through the longitudinal axis LA of the e-cigarette. Note that various components and details of the body 20, e.g. such as wiring and more complex shaping, have been omitted from FIG. 3 for reasons of clarity.

The cartomizer 30 includes an aerosol source 365; 368 arranged in an air passage 355 extending along the central (longitudinal) axis of the cartomizer 30 from the mouthpiece 35 to the connector 25A for joining the cartomizer 30 to the body 20. The aerosol source comprises a resistive heating element 365 adjacent a wicking element (liquid transport element) 368 which is arranged to transport source liquid from a reservoir of source liquid 360 to the vicinity of the heating element 365 for heating. The reservoir of source liquid 360 in this example is provided around the air passage 335 and may be implemented, for example, by providing cotton or foam soaked in source liquid. Ends of the wicking element 365 are in contact with the source liquid in the reservoir 360 so that the liquid is drawn along the wicking element to locations adjacent the extent of the heating element 365.

The general configuration of the wicking element 368 and the heating element 365 may follow conventional techniques. For example, in some implementations the wicking element 368 and the heating element 365 may comprise separate elements, e.g. a metal heating wire wound around/wrapped over a cylindrical wick, the wick, for instance, consisting of a bundle, thread or yarn of glass fibers. In other implementations, the functionality of the wicking element 368 and the heating element 365 may be provided by a single element. That is to say, the heating element 365 itself may provide the wicking function. Thus, in various example implementations, the heating element 365/wicking element 368 may comprise one or more of: a metal composite structure, such as porous sintered metal fiber media (Bekipor® ST) from Bakaert; a metal foam structure, e.g. of the kind available from Mitsubishi Materials; a multi-layer sintered metal wire mesh, or a folded single-layer metal wire mesh, such as from Bopp; a metal braid; or glass-fiber or carbon-fiber tissue entwined with metal wires. The "metal" may be any metallic material having an appropriate electric resistivity to be used in connection/combination with a battery. The resultant electric resistance of the heating element 365 will typically be in the range 0.5-5 Ohm. Values below 0.5 Ohm could be used but could potentially over-stress the battery. The "metal" could, for example, be a NiCr alloy (e.g. NiCr8020) or a FeCrAl alloy (e.g. "Kanthal") or stainless steel (e.g. AISI 304 or AISI 316).

As discussed further below, embodiments of the disclosure may rely on changes in the resistance of a heating element with temperature to identify the occurrence of fault conditions. Therefore, in accordance with certain embodiments, the resistive heating element 365 is formed from a material with a relatively high temperature coefficient of resistance. The temperature coefficient of some of the aforementioned metals is relatively low (e.g. <0.0001 $K^{-1}$ for NiCr8020 and Kanthal). Stainless steel, however, has a higher temperature coefficient. Thus in some implementations stainless steel may be a preferred material for the heating element in the context of the present disclosure, but it will of course be appreciated that other material could be used. The term "stainless steel" as used hereon may be interpreted according to the conventional terminology of metallurgy and comprises at least the SAE/AISI stainless steel series 100, 200, 300 and 400.

The heating element 365 is powered through lines 366 and 367, which are in turn connectable to opposing polarities (positive and negative, or vice versa) of the battery 210 via connector 25A and under the control of the control circuitry 550 (the details of the wiring between the power lines 366 and 367 and connector 25A are omitted from FIG. 3).

The connector 25A includes an inner electrode 375, which may be silver-plated or made of some other suitable metal. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heating element 365 in the cartomizer 30 via supply lines 366 and 367 under the control of the control circuitry 550.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
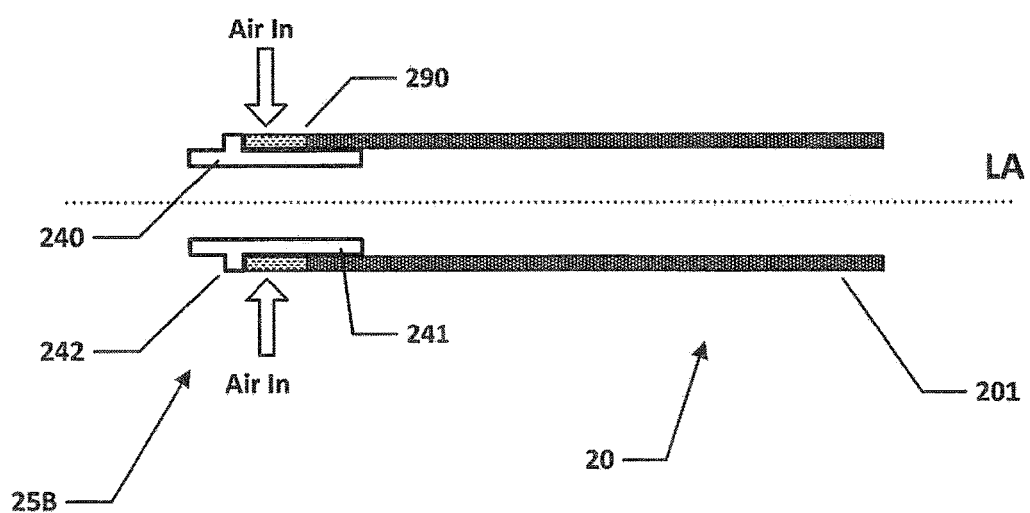
FIG. 4 is a schematic diagram showing certain aspects of one end of the main body portion of the e-cigarette of FIG. 1 in accordance with some embodiments.

FIG. 4 is a schematic diagram of certain details of the connector 25B at the end of the body 20 in accordance with some embodiments (but omitting for clarity most of the internal structure of the connector as shown in FIG. 2, such as spacer 260). In particular, FIG. 4 shows the external housing 201 of the body 20, which generally has the form of a cylindrical tube. This external housing 201 may comprise, for example, an inner tube of metal with an outer covering of paper or similar.

The body connector 240 extends from this external housing 201 of the body 20. The body connector as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette 10. Surrounding the shaft portion 241 of the body connector 240, where the shaft portion 241 does not overlap with the external housing 201, is a collar or sleeve 290, which is again in a shape of a cylindrical tube. The collar 290 is retained between the lip portion 242 of the body connector 240 and the external housing 201 of the body 20, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, for this particular example aerosol provision system, the majority of air that enters the device 10 when a user inhales flows through collar 290 and body connector 240 as indicated by the two arrows in FIG. 4.

As noted above, there is a desire for schemes for determining the occurrence of fault conditions in an aerosol provision system, and in particular the occurrence of rapid over-heating of a heating element including localized overheating (i.e. hotspots). Such overheating might, for example, be caused by a (possibly temporary) lack of source liquid for heating in the vicinity of certain parts of a heating element. Likewise it might be caused by thermally overloading the heating element when the heat flux exceeds a certain limit (e.g. around 1 $W/mm^2$). It has been previously proposed in the context of e-cigarette type devices to determine the temperature of a heating element from its resistance, e.g. in US 2014/0014126 and EP 2 316 286. However, the inventor has recognized an approach such as this is relatively insensitive to identifying the occurrence of rapid, possibly localized overheating, especially if materials with a relatively low temperature coefficient of resistance (e.g. NiCr-alloys or Kanthal) are being used for the heating element. But even the higher temperature coefficient of stainless steel may not provide the sensitivity required to determine localized overheating events (hotspots) using existing techniques. This is because measuring the temperature of a heating element from its resistance provides an indication of an average temperature for the heating element integrated along its length. For example, with a heating element having a length of 30 mm, and assuming negligible non-linear effects, it would not be possible to distinguish between a uniform temperature increase of 20° C. along the whole length of the heating element and a localized temperature increase of 200° along a 3 mm length of the heating element from a measurement of the heating elements resistance. This means an acceptable increase in temperature for a larger part of the heating element can be indistinguishable from localized overheating which might be dangerous.

Thus, an aspect of aerosol provision system in accordance with embodiments of the present disclosure makes use of changes in a heating element's resistance with temperature to determine if a fault condition has arisen, but rather than seek to determine whether a fault condition has arisen based on the resistance for the heating element, approaches in accordance with certain embodiments of the present disclosure instead determine whether a fault condition has arisen based on an observed time (t) derivative for the resistance (R) of the heating element (or a correspondingly related electrical characteristic, such as conductance, current draw, power draw or voltage drop). For example, the time derivative may in some cases be a first derivative (i.e. dR/dt) and in other cases may be a second derivative ($d^2R/dt^2$).

Figure 5:
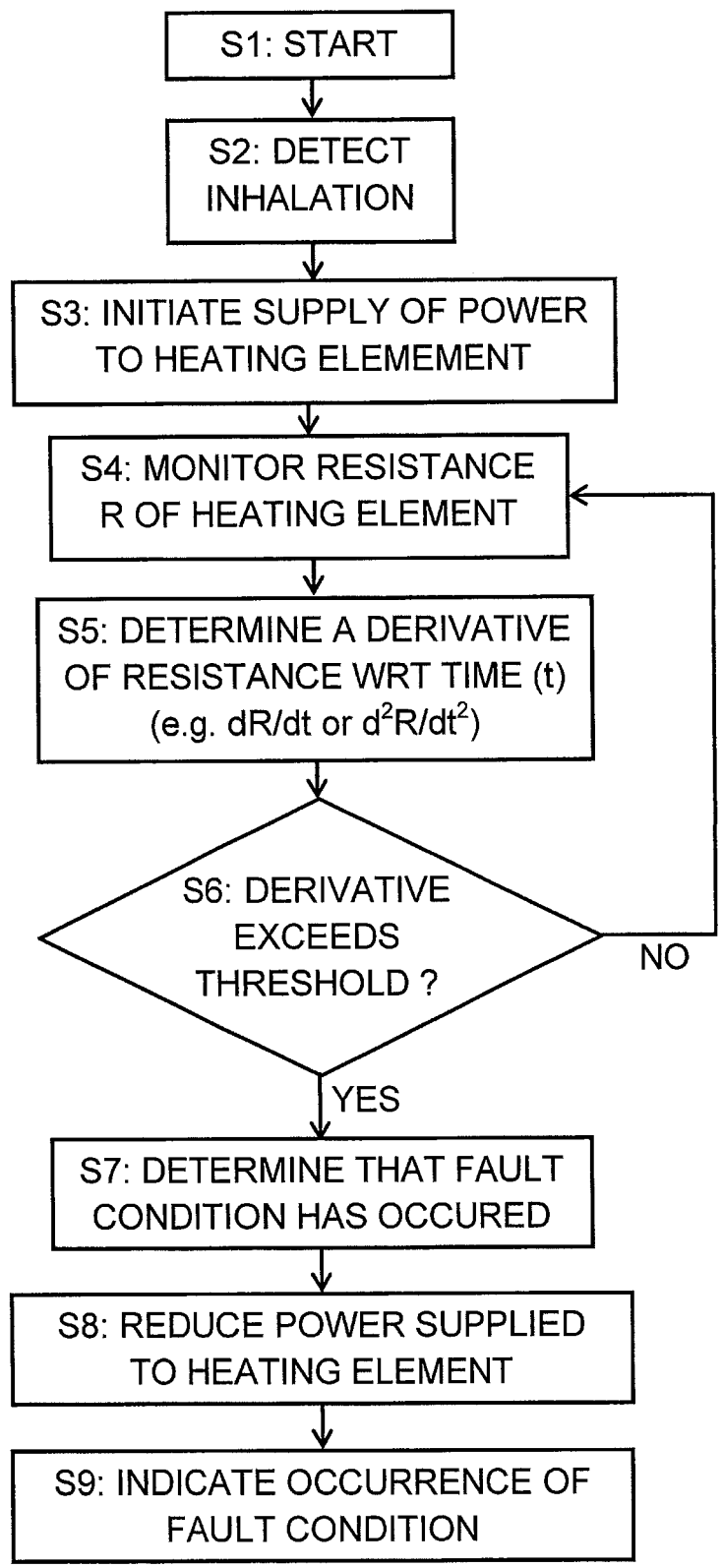
FIG. 5 is a schematic flow diagram representing a mode of operation for an electronic aerosol provision system such as an e-cigarette in accordance with some embodiments.

FIG. 5 is a flow diagram schematically representing steps of a method of operating an electronic vapor provision system in accordance with certain embodiments of the disclosure. Thus, in the context of the example the e-cigarette represented in FIGS. 1 to 4, the control circuitry 550 is configured to provide functionality in accordance with the method represented in FIG. 5.

Processing starts in S1 where it is assumed a user is in the process of using the electronic aerosol provision system 10 FIGS. 1 to 4.

In S2 the control circuitry 550 detects that the user has begun inhaling (i.e. the user has started sucking on the mouthpiece to draw air through the electronic aerosol provision system). This detection is based on signals received from the sensor 215 and may be performed in accordance with any generally conventional techniques.

In S3 the control circuitry 550 initiates the supply of electrical power to the heating element 365 to begin vaporizing source liquid from the wicking element 368 to generate an aerosol for inhalation by the user. Again, this process may be performed in accordance with conventional techniques. In particular, the specific manner in which the electrical power is supplied during normal operation (i.e. without a fault condition been deemed to have occurred) may be chosen according to a desired performance in terms of the timing and extent of aerosol generation in accordance with conventional techniques. For example, electrical power may be supplied to the heating element for a time period corresponding to the duration of a user's puff with variations in the amount of power supplied (e.g. using pulse width modulation) throughout the user's puff to provide a desired level of aerosol generation in accordance with established techniques. S4 to S6 of FIG. 5, which are discussed further below, are performed in an ongoing repeating manner during the period in which power is supplied to the heating element and aerosol is generated.

In S4 the control circuitry 550 monitors the resistance R of the heating element. This may be achieved by measuring the resistance (or a corresponding electrical parameter such as conductance, current draw, power draw or voltage drop) of the heating element at a series of discrete times, for example once every 10 ms. The process of measuring the resistance of the heating element may be performed in accordance with conventional resistance measurement techniques. That is to say, the control circuitry 550 may comprise a resistance-measuring component that is based on established techniques for measuring resistance (or a corresponding electrical parameter). In this regard the resistance-measuring component of the control circuitry 550 may be coupled to the heating element via the lines 366, 367 and the various elements of the connector components 25A, 25B. In this regard, it will be appreciated the control circuitry 550 may measure the combined resistance of the heating element and the various components that connects the control circuitry 550 to the heating element 365. However, since the resistance of the other components in the resistance path is not expected to change significantly with respect to time, this has little impact on measurements of the derivative of the resistance of the heating element with respect to time in accordance with embodiments of the disclosure described herein. It will further be appreciated the current, power or voltage drop associated with the heating element (and hence its resistance) can also be determined from measurements of an electrical characteristic (e.g. voltage or current/power draw) of another resistive element electrically coupled to the heating element, for example a power MOSFET, a shunt resistor, or even the battery itself having regard to Kirchoff's voltage law.

In S5 a derivative of resistance R with respect to time t is determined from a series of the resistance value established in S4 at different times. That is to say, the control circuitry is configured to maintain a record of previous values of R established according to the sampling period and to determine a time derivative of the established values. For example, the derivative may be a first derivative with respect to time or a second derivative with respect to time. The derivative may be determined from the established values of R in accordance with conventional numerical processing techniques for determining gradients from discrete measurements. For example, assuming a series of resistance measurements $R_0, R_1, R_2, R_3 \ldots R_{n-1}, R_n, R_{n+1} \ldots$ established according to a regular sampling period p, an initially determined indication of a first derivative at a time $t_n$ (corresponding to the time of sample $R_n$) may simply be determined according to:

$$dR/dt=(R_{n+1}-R_{n-1})/2p.$$

Similarly, an initially determined indication of a second derivative at time $t_n$ (corresponding to the time of sample $R_n$) may simply be determined according to:

$$d^2R/dt^2=(R_{n+1}+R_{n-1}-2R_n)/p^2.$$

However, it will be appreciated there are various other well-established statistical techniques for establishing a first derivative or a second derivative from a series of samples. It will further be appreciated that it is not necessary to determine an actual derivative in terms of ohms per second, but rather an indication of the derivative is sufficient. For example, with a regular sampling period, there is no need to take account of the actual time between samples as it will merely change the effective units of the determined derivative(s). In this particular example it is assumed the processing in Step S5 is based on the determination of a first derivative of resistance with respect to time (i.e. dR/dt).

In S6 the derivative established in S5 is compared with a threshold value V. In effect the threshold value is an indication of the maximum rate of change of resistance that might be expected to occur without there being any rapid overheating of the kind discussed above. If it is determined in S6 that the derivative established in S5 does not exceed the pre-defined threshold value, processing follows the path marked "NO" back to S4 where processing continues as described above. However, if it is determined in S6 that the derivative established in S5 does exceed the predefined threshold value, processing follows the path marked "YES" to S7.

In S7 it is determined that because a time derivative established in S5 has been found to exceeded the pre-defined threshold value in the comparison of S6, a fault condition is assumed to have occurred. This conclusion is based on the inventors' realization that whilst the resistance of the heating element is itself a relatively poor indicator of rapid overheating, in particular for localized overheating (hotspots) developing on the heating element, the rate of change of resistance with respect to time is a better indicator. This is because even though the overall change in resistance may be similar for both a moderate increase in temperature across the whole heating element and a more significant localized overheating event, the rate at which the temperature changes in these two cases is different. In particular, localized overheating (thermal runaway) can be expected to occur more rapidly than uniform heating of the entire heating element.

A suitable threshold value to be used in S6 may be established through calculation, modeling or experiment. For example, a sample aerosol provision system may be purposely driven into a condition that promotes hotspot development, and the derivative in resistance with respective to time may be measured as this happens. Likewise, the maximum derivative in resistance with respect to time during normal operation (i.e. without an overheating fault condition occurring) may be established. The threshold V may then be taken as a value somewhere between the maximum derivative in resistance seen during normal operation and the minimum derivative in resistance seen as a consequence of localized overheating/hotspot development, e.g. midway between these values. Aerosol provision systems of different designs will typically adopt different threshold values.

Following the determination that a fault condition has occurred in S7, processing in this example proceeds to S8 in which the power supply to the heating element is reduced, for example it may be switched off entirely. In this example the processing represented in FIG. 5 then proceeds to S9 in which an indication of the occurrence of the fault condition is raised by driving the indicator 560 to alert a user that the fault condition has occurred.

Further operation may vary according to the implementation at hand. For example, in some situations the aerosol provision system may in effect become "locked" and may not function again until a user has in effect reset the system, for example, by disconnecting and reattaching the body 20 and the cartomizer 30 (in the expectation that this may be done to refill the reservoir 360 or replace a cartomizer 30 with a new one). In some situations the aerosol provision system may only become "locked" (i.e. cease to function further) if there has been a number of fault condition detection events detected within a given time period.

For optimum performance, the derivative of resistance with respect to time may be most sensitive to the development of a localized overheating event (hotspot) for the heating element when the temperature of the heating element is otherwise considered to be temporally steady. In this regard, the processing represented in FIG. 5 may in some cases be implemented only when the temperature of the heating element is expected to remain in a steady state with the aerosol provision system operating normally. For instance, the processing may not be performed during a preheating phase, when the heating element is heated up from ambient temperature to a vaporization/boiling temperature. Such preheating may also cause rapid heating of the heating element that could present in a manner similar to a fault condition. However in other situations the processing may be performed regardless of whether or not the temperature of the heating element has stabilized. More generally, the method may be applied during periods in which aerosol is being generated and/or during a period in which electric power is being supplied to the heating element.

It will be appreciated various modifications to the apparatus and methods described above may be implemented in accordance with certain embodiments of the disclosure. For example, in addition to determining a derivative of resistance with respect to time with a view to establishing if a fault condition has arisen, the controller may also be configured to establish an effective average temperature for the heating element from the resistance measurements, for example to be used in controlling a power supply to the heating element to provide a desired degree and timing of aerosol generation in accordance with conventional techniques.

Furthermore, whilst the above-described examples have focused on the implementations in which an indication of a time derivative for resistance is derived from discrete resistance measurements (i.e. in effect using digital control circuitry), it will be appreciated an indication of the derivative of the resistance of the heating element can equally be established in the analogue domain using established analogue electronics techniques, for example by using one or more appropriately configured filters. Furthermore it will be appreciated the other steps presented in FIG. 5 could also be performed using analogue, rather than digital, electronic techniques. For example, functionality corresponding to S5 and S6 could be implemented by passing a signal indicative of the resistance of the heating element through a high-pass filter and comparing the output from the high-pass filter with a threshold level using a comparator.

As has already been noted above, it is not necessary to determine an actual derivative, e.g. in terms of ohms per second, but rather an indication of the derivative is sufficient, for example an indication of whether the derivative exceeds a particular threshold value considered to correspond with a fault condition having arisen, e.g. based on what is observed during empirical testing or modeling. For example, in one implementation the resistance of the heating element may be monitored for a given period of time during initial heater activation, for example a period of time at the beginning of a user's puff. This period of time may be considered a detection period and the device may be configured to determine if the resistance of the heater changes by more than a threshold amount over a base-line resistance value during the detection period. The base-line resistance value for normalizing subsequent measurements may correspond with a value of the heater resistance measured when the heater is cold, e.g. when a cartomizer is first connected to the body of the device or during periods between heater activation. For the sake of providing a particular concrete example, in one implementation the detection period may have a duration of 400 ms after initial heater activation and a threshold value for the rate of change of resistance considered to indicate a fault condition may be an increase of 14% over the baseline resistance measurement within this 400 ms detection period (i.e. an increase of 0.14 in normalized resistance). Thus, if a measurement of resistance during the detection period indicates an increase there is change in resistance which is greater than 14% of the baseline resistance value within the 400 ms detection period, this indicates the rate of change of resistance is greater than the threshold for indicating a fault and the device may respond accordingly.

Thus, there has been described an aerosol provision system, such as an electronic cigarette, comprises a heating element for generating an aerosol from a source liquid and control circuitry for controlling a supply of electrical power from a power supply, such as a battery/cell, to the heating element. The control circuitry is configured to measure an indication of a derivative of an electrical characteristic of the heating element with respect to time, for example a first time derivative or a second time derivative of a resistance of the heating element (or a related parameter, such as conductance, current draw, power draw or voltage drop). Based on the measured time derivative, the control circuitry is configured to determine whether or not a fault condition, e.g. localized heating of the heating element, has arisen for the electronic aerosol provision system. The overall change in the electrical characteristic for the heating element caused by the localized heating may be small and so difficult to reliably identify, but the rate at which the change occurs can be expected to be relatively high, which can mean the time derivative of the local characteristic is more reliable indicator of the occurrence of the fault condition.

While the above described embodiments have in some respects focused on some specific example aerosol provision systems, it will be appreciated the same principles can be applied for aerosol provision systems using other technologies. That is to say, the specific manner in which various aspects of the aerosol provision system which are not directly relevant to establishing whether a fault condition has arisen for a heating element in accordance with the approaches described herein is not significant to the principles underlying certain embodiments. For example, configurations based on the systems disclosed in US 2011/0226236, could be used in other implementations.

In order to address various issues and advance the art, this disclosure shows by way of illustration various embodiments in which that which is claimed may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An electronic aerosol provision system comprising:
a heating element for generating an aerosol from a source liquid, the heating element having a resistance of between 0.5 and 5.0 ohms; and
control circuitry for controlling a supply of electrical power from a power supply to the heating element, and wherein the control circuitry is further configured to:
determine an indication of a derivative of an electrical characteristic of the heating element with respect to time; and
determine whether or not an overheating fault condition for the electronic aerosol provision system has arisen based on the determined indication of the derivative of the electrical characteristic of the heating element with respect to time by comparing the indication of the derivation of the electrical characteristic of the heating element with a predefined threshold value.

2. The electronic aerosol provision system of claim 1, wherein the indication of the derivative of the electrical characteristic of the heating element with respect to time comprises an indication of a first derivative of the electrical characteristic of the heating element with respect to time.

3. The electronic aerosol provision system claim 1, wherein the indication of the derivative of the electrical characteristic of the heating element with respect to time comprises an indication of a second derivative of the electrical characteristic of the heating element with respect to time.

4. The aerosol provision system of claim 1, wherein the heating element comprises a resistive heating element.

5. The aerosol provision system of claim 4, wherein the resistive heating element comprises stainless steel.

6. The electronic aerosol provision system of claim 1, wherein the electrical characteristic of the heating element is based on one or more characteristics selected from the group comprising: an electrical resistance associated with the heating element; an electrical conductance associated with the heating element; a current draw associated with the heating element; a power draw associated with the heating element, a voltage drop associated with the heating element, and a voltage drop associated with another resistive element electrically coupled to the heating element.

7. The electronic aerosol provision system of claim 1, wherein the control circuitry is further configured to determine an indication of a temperature of the heating element from measurements of the electrical characteristic.

8. The electronic aerosol provision system of claim 1, wherein the overheating fault condition is associated with a sudden rise in temperature of at least a portion of the heating element.

9. The electronic aerosol provision system of claim 1, wherein the overheating fault condition is associated with occurrence of glowing of at least a portion of the heating element.

10. The electronic aerosol provision system of claim 1, wherein the control circuitry is configured to determine the overheating fault condition has arisen if the magnitude of the indication of the derivative of the electrical characteristic of the heating element with respect to time exceeds the predefined threshold value.

11. The electronic aerosol provision system of claim 1, wherein the control circuitry is configured to determine the indication of the derivative of the electrical characteristic of the heating element with respect to time during a period in which the temperature of the heating element is considered to be temporally steady.

12. The electronic aerosol provision system of claim 1, wherein the control circuitry is configured to determine the indication of the derivative of the electrical characteristic of the heating element with respect to time during a period in which aerosol is being generated by the heating element.

13. The electronic aerosol provision system of claim 1, wherein the control circuitry is configured to determine the indication of the derivative of the electrical characteristic of the heating element with respect to time during a period in which electric power is being supplied to the heating element.

14. The electronic aerosol provision system of claim 1, wherein the control circuitry is further configured to reduce the supply of power to the heating element if it is determined the fault condition has arisen.

15. The electronic aerosol provision system of claim 14, wherein the control circuitry is further configured to stop the supply of power to the heating element if it is determined the fault condition has arisen.

16. The electronic aerosol provision system of claim 1, wherein the control circuitry is further configured to activate a warning indicator if it is determined the fault condition has arisen.

17. The aerosol provision system of claim 1, wherein the aerosol provision system comprises the source liquid, and the source liquid includes nicotine.

18. The aerosol provision system of claim 1, further comprising a reservoir of source liquid and a liquid transport element arranged to transport a portion of the source liquid to the vicinity of the heating element for heating to generate the aerosol.

19. The aerosol provision system of claim 1, further comprising the power supply in the form of a battery or cell.

20. A method of operating an electronic aerosol provision system comprising a heating element for generating an aerosol from a source liquid and control circuitry for controlling a supply of electrical power from a power supply to the heating element, wherein the method comprises:
  determining an indication of a derivative of an electrical characteristic of the heating element with respect to time; and
  determining whether or not an overheating fault condition for the electronic aerosol provision system has arisen based on the determined indication of the derivative of the electrical characteristic of the heating element with respect to time by comparing the indication of the derivative of the electrical characteristic of the heating element with respect to time with a predefined threshold value,
  wherein the heating element has a resistance of between 0.5 and 5.0 ohms.

* * * * *

UNITED STATES PATENT AND TRADEMARK OFFICE
CERTIFICATE OF CORRECTION

PATENT NO. : 11,413,410 B2
APPLICATION NO. : 15/506594
DATED : August 16, 2022
INVENTOR(S) : Helmut Buchberger, Colin Dickens and Rory Fraser Page 1 of 1

It is certified that error appears in the above-identified patent and that said Letters Patent is hereby corrected as shown below:

On the Title Page

In Column 2, item (57), under Abstract, Line 10, delete "characteristic for" and insert -- characteristic of --.

In the Drawings

Sheet 3 of 3, FIG. 5, for Step S3", Line 2, delete "ELEMEMENT" and insert -- ELEMENT --.

Sheet 3 of 3, FIG. 5, for Step S7", Line 2, delete "OCCURED" and insert -- OCCURRED --.

In the Claims

In Column 14, Claim 3, Line 16, delete "system claim" and insert -- system of claim --.

In Column 14, Claim 4, Line 22, delete "The aerosol" and insert -- The electronic aerosol --.

In Column 14, Claim 5, Line 24, delete "The aerosol" and insert -- The electronic aerosol --.

In Column 15, Claim 17, Line 15, delete "The aerosol" and insert -- The electronic aerosol --.

In Column 15, Claim 18, Line 18, delete "The aerosol" and insert -- The electronic aerosol --.

In Column 16, Claim 19, Line 1, delete "The aerosol" and insert -- The electronic aerosol --.

Signed and Sealed this
Twenty-sixth Day of November, 2024

Katherine Kelly Vidal
*Director of the United States Patent and Trademark Office*